United States Patent
Gielen et al.

(10) Patent No.: US 6,407,265 B2
(45) Date of Patent: Jun. 18, 2002

(54) TIN POLYOXAALKANECARBOXYLATES AND COMPOSITIONS CONTAINING THEM

(75) Inventors: Marcel Gielen, Wezembeek-Oppem; Rudolph Willem, Vilvoorde; Monique Biesemans, St. Amands, all of (BE); Martine Kemmer, Helmdange (LU); Dick de Vos, Oegstgeest (NL)

(73) Assignee: Pharmachemie B.V., Haarlem (NL)

( * ) Notice: Subject to any disclaimer, the term of this patent is extended or adjusted under 35 U.S.C. 154(b) by 0 days.

(21) Appl. No.: 09/770,299

(22) Filed: Jan. 29, 2001

Related U.S. Application Data

(63) Continuation of application No. PCT/NL98/00429, filed on Jul. 29, 1998.

(51) Int. Cl.$^7$ .......................... C07D 321/00; C07F 7/24; C07C 69/66
(52) U.S. Cl. .......................... 549/351; 556/106; 560/186
(58) Field of Search .................. 549/351; 556/106; 560/86; 514/450, 493, 513

(56) References Cited

U.S. PATENT DOCUMENTS 5,608,058 A * 3/1997 Tanaka et al. .............. 549/351

FOREIGN PATENT DOCUMENTS

| EP | 0484596 | 11/1990 | ................. 556/106 |
| EP | 0538517 | 4/1993 | ................. 556/106 |
| EP | 0700921 | 9/1994 | ................. 556/106 |

OTHER PUBLICATIONS

"Tin Based Antitumour Drugs", M. Gielen, *Coord. Chem. Rev.,* 1996.
"Reviews on Silicon, Germanium Tin and Lead Compounds", G. Atassi, 1985.
"In Vitro Antitumour Activity of Organotin . . . ", M. Gielen, et al., 1990.
"Comparison of the Sulforhodamine B Protein", Y.P. Keepers, et al., 1991.
"The Preparation of Organotin Alkoxides", A. G. Davies, et al., 1991.
"New Colorimetric Cytotoxicity Assay", P. Skehan, et al., 1989.
"Di–N–Butyltin and Diethyltin Monoflourobenzoates . . . ", M. Gielen, et al., 1993.

* cited by examiner

*Primary Examiner*—Alan L. Rotman
*Assistant Examiner*—Raymond Covington
(74) *Attorney, Agent, or Firm*—Browdy and Neimark

(57) ABSTRACT

Tin polyaalkanecarboxylates having the formula $[(R^1_p R^2_q Sn)_r O_s]_t$ wherein $R^1$ represents $C_1$–$C_6$ alkyl, branched or straight, substituted or not by one or more hydroxyl groups or halogen atoms, or a phenyl group, substituted or not by one or more hydroxyl groups or halogen atoms, $R_2$ is carboxylic residue selected from (I), (II), (III) or (IV); and p, q, r, s and t have the following meanings: P=3, q=1, r=1, s=) and t=1, p=2, q=2, r=1, s=0, and t=1, p=2, q=1, r=2, s=1 and t=2, have anti-tumor activity.

4 Claims, No Drawings

TIN POLYOXAALKANECARBOXYLATES AND COMPOSITIONS CONTAINING THEM

REFERENCE TO RELATED APPLICATION

The present application is the Continuation of prior international application PCT/NL98/00429, filed Jul. 29, 1998, which designated the United States, and which international application was published under PCT Article 21 (2)in the English language. The entire contents of said PCT/NL98/00429 are hereby incorporated by reference.

The invention relates to novel tin polyoxaalkanecarboxylates and to anti-tumour compositions containing such compounds.

The anti-tumour activity of tin compounds is known; it is also known that the anti-tumour activity of tin compounds could be enhanced by increasing their solubility in water.

The invention now provides water-soluble tin compounds which show strong in vitro anti-tumour activities against a broad spectrum of tumours, as appears from the experimental part, disclosed hereinafter.

More specifically the invention relates to tin polyoxaalkanecarboxylates having the formula

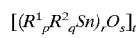

wherein $R^1$ represents $C_1-C_6$ alkyl, branched or straight, substituted or not by one or more hydroxyl groups or halogen atoms, or a phenyl group, substituted or not by one or more hydroxyl groups or halogen atoms, $R^2$ is a carboxylic residue selected from:

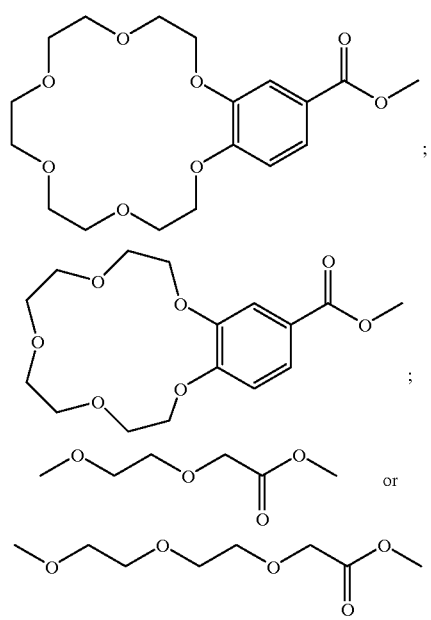

and p, q, r, s and t have the following meanings:
p=3, q=1, r=1, s=0 and t=1;
p=2, q=2, r=1, s=0 and t=1;
p=2, q=1, r=2, s=1 and t=2.

According to a preferred embodiment of the invention, represents $R^1$ a phenyl group or a n-butyl group in a compound having formula (1), (2) or (3).

The compounds according to the invention can be synthesized by effecting a condensation reaction between a carboxylic acid having formula

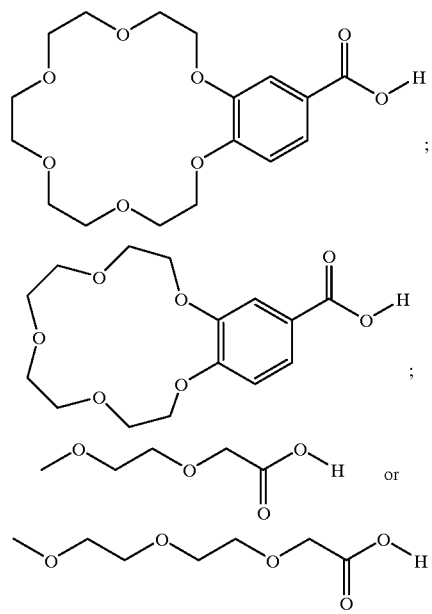

with triaryltin hydroxide, trialkyltin acetate or dialkyltin oxide, preferably triphenyltin hydroxide, tri-n-butyltin acetate or di-n-butyltin oxide, according to the following reaction schemes:

a) 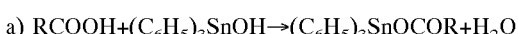

b) 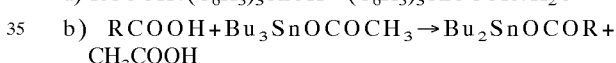

c) 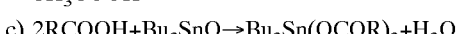

d) 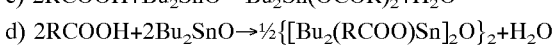

Different media and methods can be used to synthesize such derivatives 1) the condensation can be performed in toluene/ethanol. The water formed during the condensation is eliminated by azeotropic distillation (Dean-Stark funnel)
2) benzene can be used instead of toluene/ethanol
3) these compounds can also be prepared by a two-step procedure, dibutyltin oxide being first condensed with n-propanol to yield tetrabutyldipropoxydistannoxane:

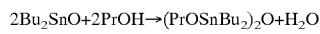

In a second step, the carboxylic acid is added at room temperature to this tetrabutyldipropoxydistannoxane in the desired molar ratio.

The compounds synthesized by one of these methods were characterized by elemental analysis, $^1H$, $^{13}C$ and $^{117}Sn$ NMR, electrospray mass spectrometry and $^{119m}Sn$ Mössbauer spectroscopy. Chromatography on Sephadex LH-20 proved to be a very efficient method to separate 3 (or 7) from 4 (or 8), or 11, 12, 15 and 16 from the starting carboxylic acid.

The structures of the compounds synthesized are depicted below

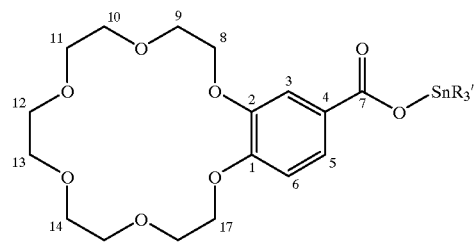
R' = C$_6$H$_5$ 1
R' = CH$_2$CH$_2$CH$_2$CH$_3$ 2
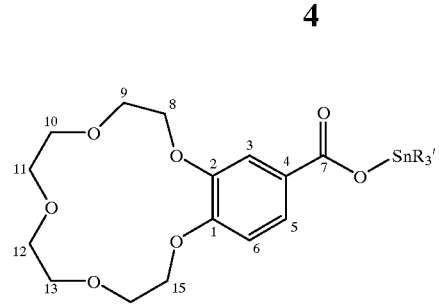
R' = C$_6$H$_5$ 5
R' = CH$_2$CH$_2$CH$_2$CH$_3$ 6
3
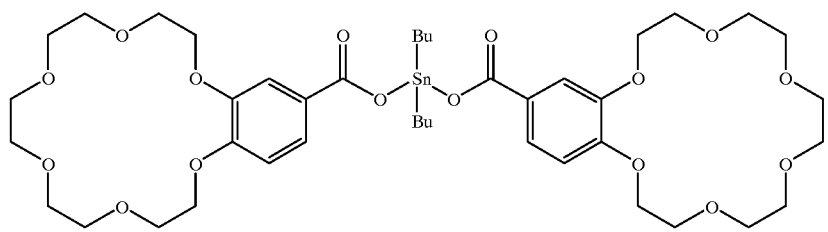
4
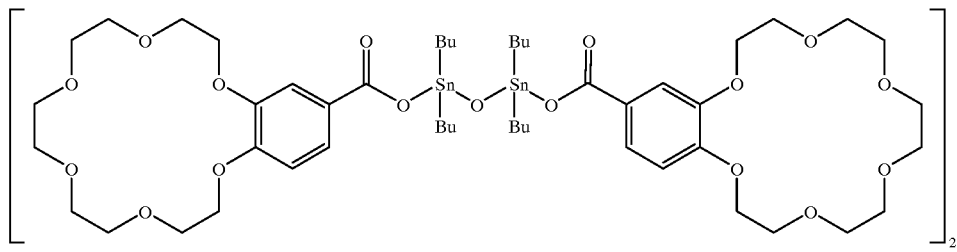
7
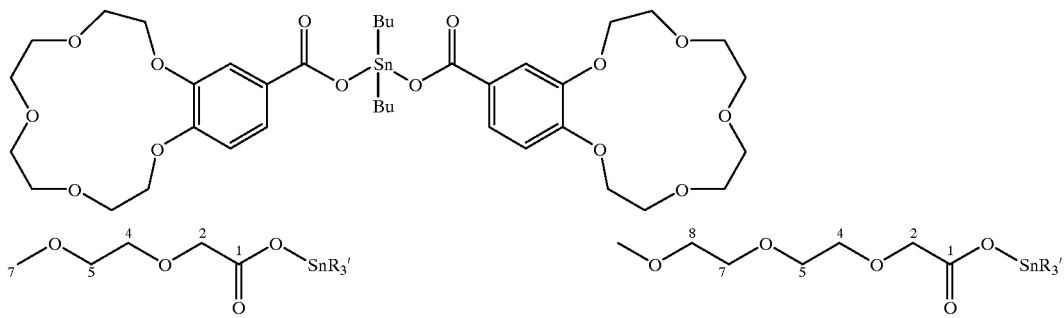
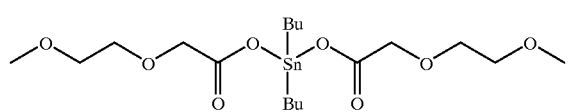
R' = C$_6$H$_5$ 8
R' = CH$_2$CH$_2$CH$_2$CH$_3$ 9
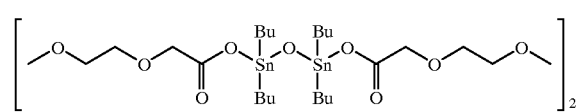
R' = C$_6$H$_5$ 12
R' = CH$_2$CH$_2$CH$_2$CH$_3$ 13
10
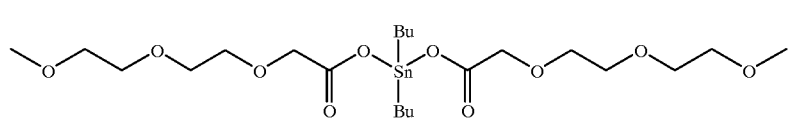
11
14
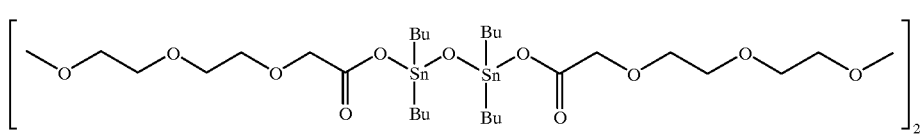
15

GENERALITIES AND ABBREVIATIONS

NMR spectra: CDCl$_3$ solutions; $^1$H and $^{13}$C chemical shifts δ in ppm vs. TMS, homonuclear coupling constants in Hz, in parentheses; Mössbauer parameters (quadrupole splitting QS, isomers shift IS, and band widths Γ$_1$ and Γ$_2$) in mm/s; s: singlet; d: doublet; dd: doublet of doublets; m: complex pattern; t: triplet; tq: triplet of quartets; ψs, pseudo-singlet.

Electrospray mass spectra: positive monoisotopic ions ($^{12}$C, $^1$H, $^{16}$O, $^{23}$Na, $^{39}$K, $^{120}$Sn). Na and/or K are already present in the electrospray mass spectra of the starting carboxylic acids.

Charaterization of Compounds 1 to 15

Compound 1: triphenyltin 4,7,10,13,16,19-hexaoxadicyclo[16.4.0]dicosa-1,3 (20),21-triene-1-carboxylate prepared according to method 1, 10 h of reflux, recrystallized from diethyl ether/hexane, m.p. 110–112° C., yield 98%, elemental analysis: exp. (calc. for C$_{35}$H$_{38}$SnO$_8$): C: 60.2 (59.60); H: 5.5 (5.43); $^1$H NMR: 7.7–7.8, m, H(o) & H(5); 7.62, d ($^4$J($^1$H–$^1$H)=2), H(3); 7.4–7.5, m, H(m) & H(p); 6.91, d ($^3$J($^1$H–$^1$H)=9), H(6); 4.1–4.3, m, H(8) & H(17); 3.8–4.0, m, H(9) & H(16); 3.6–3.8, m, H(10), H(11), H(14) & H(15); 3.67, ψs, H(12) & H(13); $^{13}$C NMR: 172.7, C(7); 152.9, C(1); 148.0, C(2); 138.5, C(i); 137.0, C(o) $^2$J($^{117/119}$Sn–$^{13}$C)=47/49; 130.2, C(p) $^4$J($^{117/119}$Sn—$^{13}$C)=13; 129.0, C(m) $^3$J($^{117/119}$Sn–$^{13}$C)=61/63; 125.1, C(5); 122.8, C(4); 114.9, C(3); 111.7, C(6); 70.80 & 70.77, C(10) & C(15); 70.71 & 70.66, C(12) & C(13); 70.53, 70.51, 69.4, 69.2, 68.8 & 68.6, C(8), C(9), C(11), C(14), C(16) & C(17); $^{117}$Sn NMR: –115.7; electrospray MS: M+K$^+$(m/z=745), 14%; M+Na$^+$, 100%; Mössbauer: QS: 2.26; IS: 0.55; Γ$_1$: 1.34; Γ$_2$: 1.32.

Compound 2: tri-n-butyltin 4,7,10,13,16,19-hexaoxadicyclo[16.4.0]dicosa-1,3(20),21-triene-1-carboxylate prepared according to method 1, 4 h of reflux, recryst. hexane/chloroform, m.p. 45–47° C., yield 80%, elemental analysis: exp. (calc. for C$_{29}$H$_{50}$SnO$_8$.H$_2$O): C: 52.5 (52.50); H: 8.3 (7.90); $^1$H NMR: 7.63, dd ($^3$J($^1$H–$^1$H)=8; $^4$J($^1$H–$^1$H)=2), H(5); 7.54, d ($^4$J($^1$H–$^1$H)=2), H(3); 6.82, d ($^3$J($^1$H–$^1$H)=8), H(6); 4.1–4.3, m, H(8) & H(17); 3.8–4.0, m, H(9) & H(16); 3.6–3.8, m, H(10), H(11), H(14) & H(15); 3.65, ψs, H(12) & H(13);~2, HOH; 1.6–1.7, m H(β); 1.2–1.3, m, H(α) & H(γ); 0.89, t ($^3$J($^1$H–$^1$H)=7), H(δ); $^{13}$C NMR: 171.4, C(7); 152.2, C(1); 148.1, C(2); 125.0, C(4); 124.2, C(5); 115.0, C(3); 112.1, C(6); 70.96 & 70.84, C(10) & C(15); 70.77 & 70.73, C(12) & C(13); 70.66, 70.61, 69.5, 69.4, 68.9 & 68.8, C(8), C(9), C(11), C(14), C(16) & C(17); 27.9, C(β) $^2$J($^{117/119}$Sn–$^{13}$C)=20; 27.0, C(γ) $^3$J($^{117/119}$Sn–$^{13}$C)=62/65; 16.6, C(α) $^1$J($^{117/119}$Sn–$^{13}$C)=341/358; 13.7, C(δ); $^{117}$Sn NMR: 108.2; electrospray MS: M+Na$^+$ (m/z=669), 6%; M+H$_2$O+H$^+$, 9%; M+H$^+$, 11%; Mössbauer: QS: 3.40; IS: 1.39; Γ$_1$: 0.72; Γ$_2$: 0.85.

Compound 3: di-n-butyltin bis[4,7,10,13,16,19-hexaoxadicyclo[16.4.0]dicosa-1,3(20),21-triene-1-carboxylate, prepared according to method 1, 6 h of reflux, recryst. hexane/chloroform, m.p. 125–127° C., yield 96%, elemental analysis: exp. (calc. for C$_{42}$H$_{64}$SnO$_{16}$): C: 53.5 (53.46); H: 7.1 (6.84); $^1$H NMR: 7.73, d ($^3$J($^1$H–$^1$H)=8), H(5); 7.58, s, H(3); 6.86, d ($^3$J($^1$H–$^1$H)=8), H(6); 4.1–4.3, m, H(8) & H(17); 3.8–4.0, m, H(9) & H(16); 3.6–3.8, m, H(10), H(11), H(14) & H(15); 3.65, ψs, H(12) & H(13); 1.7–1.8, m, H(β) & H(α); 1.37, tq, ($^3$J($^1$H–$^1$H)=7, $^3$J($^1$H–$^1$H)=7), H(γ); 0.86, t ($^3$J($^1$H–$^1$H)=7), H(δ); $^{13}$C NMR: 175.7, C(7); 153.0, C(1); 148.3, C(2); 124.9, C(5); 122.7, C(4); 115.3, C(3); 112.3, C(6); 70.9, C(10) & C(15); 70.81 & 70.76, C(12) & C(13); 70.73 & 70.67, 69.5, 69.4, 69.2 & 69.0, C(8), C(9), C(11), C(14), C(16) & C(17); 26.7, C(β) $^2$J($^{117/119}$Sn–$^{13}$C)=33; 26.3, C(γ) $^3$J($^{117/119}$Sn–$^{13}$C)=95; 25.4, C(α) $^1$J($^{117/119}$Sn–$^{13}$C)=569/596; 13.5, C(δ); $^{117}$Sn NMR: –156.2; electrospray MS: M+Na$^+$ (m/z 967), 100%; Mössbauer: QS: 3.41; IS: 1.44; ψ$_1$: 10.94; ψ$_2$: 0.94.

Compound 4: bis{di-n-butyl-[4,7,10,13,16,19-hexaoxadicyclo[16.4.0]dicosa-1,3(20),21-triene-1-carboxylato]tin}oxide, prepared according to method 3

12 h of reflux, Sephadex LH-20, elution with chloroform/methylene chloride; recryst. hexane/chloroform, m.p. 96–98° C., yield 90%, elemental analysis: exp. (calc. for C$_{100}$H$_{164}$Sn$_4$O$_{34}$): C: 50.0 (50.35); H: 7.1 (6.94); $^1$H NMR: 7.54, d ($^3$J($^1$H–$^1$H)=8), H(5); 7.49, s, H(3); 6.84, d ($^3$J($^1$H–$^1$H)=8), H(6); 4.1–4.3, m, H(8) & H(17); 3.8–4.0, m, H(9) & H(16); 3.6 3.8, m, H(10), H(11), H(14) & H(15); 3.62, ψs, H(12) & H(13); 1.6–1.8, m, H(β); 1.4–1.6, m, H(α); 1.1–1.4, m, H(γ); 0.7–0.9, m, H(δ); $^{13}$C NMR: 172.6, C(7); 152.5, C(1); 148.3, C(2); 126.3, C(4); 124.0, C(5); 115.3, C(3); 112.4, C(6); 70.8, C(10) & C(15); 70.7 & 70.6, C(12) & C(13); 70.6, 70.5, 69.42, 69.35, 69.1 & 68.9, C(8), C(9), C(11), C(14), C(16) & C(17); 26.7 & 26.6, C(β); 27.6 & 27.4, C(γ); 29.5 & 28.3, C(α); 13.5 & 13.4, C(δ); $^{117}$Sn NMR: –213.0 & –217.3; electrospray MS: M/2+K$^+$ (m/z=1233), 11%:; Mössbauer: QS: 3.36; IS: 1.27; Γ$_1$: 0.96; Γ$_2$: 0.99.

Compound 5: triphenyltin 4,7,10,13,16-pentaoxadicyclo[13.4.0]cosa-1,3 (17),18-triene-1-carboxylate, prepared according to method 2, 48 h of reflux, recryst. hexane, m.p.: 130–131° C., yield 95%, elemental analysis: exp. (calc. for C$_{33}$H$_{34}$SnO$_7$.1 H$_2$O): C: 58.4 (58.34); H: 5.7 (5.35); $^1$H NMR: 7.7–7.8, m, H(o) & H(5); 7.60, d ($^4$J($^1$H–$^1$H)=2), H(3); 7.4–7.5, m, H(m) & H(p); 6.82, d ($^3$J($^1$H–$^1$H)=8), H(6); 4.1–4.2, m, H(8) & H(15); 3.8–3.9, m, H(9) & H(14); 3.73, ψs, H(10), H(11), H(12) & H(13);~2, HOH; $^{13}$C NMR: 172.8, C(7); 153.1, C(1); 148.3, C(2); 138.7, C(i); 136.9, C(o) $^2$J($^{117/119}$Sn–$^{13}$C)=47/49; 130.1, C(p) $^4$J($^{117/119}$Sn—$^{31}$C)=13; 128.9, C(m) $^3$J($^{117/119}$Sn–$^{13}$C)=62/65; 125.2, C(5); 123.3, C(4); 115.7, C(3); 112.1, C(6); 70.95 & 70.92, C(8) & C(15); 70.31 & 70.23, C(9) & C(14); 69.3, 69.2, 69.9 & 68.5, C(10), C(11), C(12) & C(13); $^{117}$Sn NMR: –116.3; electrospray MS: M+K$^+$ (m/z=701, 67%); M+Na$^+$, 73%; Mössbauer: QS: 2.77; IS: 1.23; Γ$_1$: 0.94; Γ$_2$: 0.88.

Compound 6: tri-n-butyltin 4,7,10,13,16-pentaoxadicyclo[13.4.0]cosa-1,3 (17),18-triene-1-carboxylate, prepared according to method 2, 25 h of reflux, Sephadex LH-20, elution with chloroform/methylene chloride, liquid; yield 90%; elemental analysis: exp. (calc. for C$_{27}$H$_{46}$SnO$_7$.½ H$_2$O): C: 53.1 (53.14); H: 7.8 (7.77); $^1$H NMR: 7.63, dd ($^3$J($^1$H–$^1$H)=8; $^4$J($^1$H–$^1$H)=2), H(5); 7.54, d ($^4$J($^1$H–$^1$H)=2), H(3); 6.82, d ($^3$J($^1$H–$^1$H)=8), H(6); 4.1–4.2, m, H(8) & H(15); 3.8–3.9, m, H(9) & H(14); 3.73, ψs, H(10), H(11), H(12) & H(13); 1.6–1.7, m, H(β); 1.2–1.4, m, H(α) & H(γ); 0.89, t ($^3$J($^1$H–$^1$H)=7), H(δ); $^{13}$C NMR: 171.4, C(7); 152.5, C(1); 148.4, C(2); 125.1, C(4); 124.4, C(5); 115.5, C(3); 112.3, C(6); 71.2, C(8) & C(15); 70.57 & 70.52, C(9) & C(14); 69.6, 69.5, 69.1 & 68.9, C(10), C(11), C(12) & C(13); 27.9, C(β) $^2$J($^{117/119}$Sn–$^{13}$C)=20; 27.0, C(γ) $^3$J($^{117/119}$Sn–$^{13}$C)=62/65; 16.6, C(α) $^1$J($^{117/119}$Sn–$^{13}$C)=350/362; 13.6, C(δ); $^{117}$Sn NMR: 107.4; electrospray MS: M+Na$^{+(m/z}$=625), 5%; M+NH$_4^+$, 9%; Mössbauer: QS: 3.29; IS: 1.45; Γ$_1$: 0.94; Γ$_2$: 0.88.

Compound 7: di-n-butyltin bis[4,7,10,13,16-pentaoxadicyclo[13.4.0]cosa-1,3(17),18-triene-1-carboxylate], prepared according to methode 2, 48 h of reflux, recrystallized from petroleum ether/methylene chloride, m.p.: 130–132° C.; yield 98%; elemental analysis: exp. (calc. for $C_{38}H_{56}SnO_{14}$): C: 53.9 (53.35); H: 6.7 (6.60); $^1$H NMR: 7.74, dd ($^3J(^1H-^1H)=8$, $^4J(^1H-^1H)=2$), H(5); 7.59, d ($^4J(^1H-^1H)=2$), H(3); 6.86, d ($^3J(^1H-^1H)=8$), H(6); 4.1–4.2, m, H(8) & H(15); 3.8–4.0, m, H(9) & H(14); 3.75, ψs, H(10), H(11), H(12) & H(13); 1.7–1.8, m, H(β) & H(α); 1.38, tq ($^3J(^1H-^1H)=7$, $^3J(^1H-^1H)=7$), H(γ); 0.86, t ($^3J(^1H-^1H)=7$), H(δ); $^{13}$C NMR: 175.8, C(7); 153.5, C(1); 148.5, C(2); 125.0, C(5); 122.9, C(4); 115.4, C(3); 112.2, C(6); 71.11 & 71.09, C(8) & C(15); 70.39 & 70.31, C(9) & C(14); 69.4, 69.2, 69.0 & 68.6, C(10), C(11), C(12) & C(13); 26.7, C(β), $^2J(117/119Sn-^{13}C)=34$; 26.4, C(γ), $^3J(^{117/119}Sn-^{13}C)=103$; 25.5, C(α), $^1J(^{117/119}Sn-^{31}C)=561/588$; 13.6, C(δ); $^{117}$Sn NMR: –156.8; electrospray MS: M+Na$^+$ (m/z=879), 27%, M+K$^+$, 27%; Mössbauer: QS: 3.28; IS: 1.41; $\Gamma_1$: 0.92; $\Gamma_2$: 0.93.

Compound 8: triphenyltin 3,6-diheptanoate, prepared according to method 2, 8 h of reflux, recrystallized from hexane/chloroform, m.p.: 100–102° C., yield 95%, elemental analysis: exp. (calc. for $C_{23}H_{24}SnO_4$): C: 57.4 (57.18); H: 4.7 (5.01); $^1$H NMR: 7.7–7.8, m. H(o); 7.4–7.5, m, H(m) & H(p); 4.25, s, H(2); 3.7–3.8, m, H(4); 3.5–3.6, m, H(5); 3.35, s, H(7); $^{13}$C NMR: 176.5, C(1); 137.7, C(i); 136.8, C(o) $^2J(^{117/119}Sn-^{13}C)=49$; 130.2, C(p) $^4J(^{117/119}Sn-^{13}C)=13$; 128.9, C(m) $^3J(^{117/119}Sn-^{13}C)=62/65$; 72.0, C(5); 70.6, C(4); 69.0, C(2); 59.0, C(7); $^{117}$Sn NMR: –100.0; electrospray MS: M+Na$^+$ (m/z=507), 5%, M+H$^+$, 2%; Mössbauer: QS: 3.60; IS: 1.24; $\Gamma_1$: 0.85; $\Gamma_2$: 0.79.

Compound 9: tri-n-butyltin 3,6-diheptanoate, prepared according to methode 2, 8 h of reflux, Sephadex LH-20, elution with methylene chloride, liquid, yield 95% elemental analysis: exp. (calc. for $C_{17}H_{36}SnO_4.\frac{1}{2}H_2O$): C: 47.4 (47.27); H: 8.6 (8.63);; $^1$H NMR: 4.09, S, H(2); 3.6–3.7, m, H(4); 3.5–3.6, m, H(5); 3.36, S, H(7);~2, HOH; 1.5–1.6, m, H(β); 1.2–1.4, m, H(α) & H(γ); 0.88, t ($^3J(^1H-^1H)=7$), H(δ); $^{13}$C NMR: 175.2, C(1); 71.9, C(1); 70.4, C(4); 69.0, C(2); 59.0, C(7); 27.8, C(β) $^2J(^{117/119}Sn-^{13}C)=20$; 27.1, C(γ) $^3J(^{117/119}Sn-^{13}C)=64/67$; 16.6, C(α) $^1J(^{117/119}Sn-^{13}C)=338/355$; 13.7, C(8); $^{117}$Sn NMR: 120.7; electrospray MS: M+Na$^+$ (m/z=447), 7%; Mössbauer: QS: 3.81; IS: 1.47; $\Gamma_1$: 1.15; $\Gamma_2$: 1.14.

Compound 10: di-n-butyltin bis(3,6-diheptanoate), prepared according to method 3, 12 h of reflux, liquid, yield 98%; elemental analysis: exp. (calc. for $C_{18}H_{36}SnO_8$): C: 43.4 (43.31); H: 7.5 (7.27); $^1$H NMR: 4.16, s, H(2); 3.6–3.8, m, H(4); 3.5–3.6, m, H(5); 3.36, s, H(7); 1.6–1.7, m, H(β) & H(α); 1.34, tq ($^3J(^1H-^1H)=7$, $^3J(^1H-^1H)=7$), H(γ); 0.87, t ($^3J(^1H-^1H)=7$), H(δ); $^{13}$C NMR: 178.3, C(1); 71.8, C(5); 70.7, C(4); 68.6, C(2); 59.0, C(7); 26.5, C(β) $^2J(^{117/119}Sn-^{13}C)=34$; 26.3, C(γ) $^3J(^{117/119}Sn-^{13}C)=98/102$; 25.7, C(α) $^1J(^{117/119}Sn-^{13}C)=538/567$; 13.4, C(δ); $^{117}$Sn NMR: –124.7; electrospray MS: M+Na$^+$ (m/z=523), 77%; M+K$^+$, 13%; Mössbauer: QS: 3.90; IS: 1.44; $\Gamma_1$: 1.28; $\Gamma_2$: 1.02.

Compound 11: bis[di-n-butyl(3,6-dioxaheptanoato)tin] oxide, prepared according to method 3, 12 h of reflux, Sephadex LH-20, elution with methylene chloride, liquid, yield 80%; elemental analysis: exp. (calc. for $C_{52}H_{108}Sn_4O_{18}.2H_2O$): C: 40.7 (40.76); H: 7.2 (7.37); $^1$H NMR: 3.95, s, H(2); 3.6–3.7, m, H(4); 3.5–3.6, m, H(5); 3.34, s, H(7);~2, HOH; 1.5–1.7, m, H(β); 1.3–1.5, m, H(α); 1.30, tq, ($^3J(^1H-^1H)=7$, $^3J(^1H-^1H)=7$), H(γ); 0.86, m, H(δ); $^{13}$C NMR: 174.9, C(1); 71.8, C(5); 70.2, C(4); 69.8, C(2); 58.9, C(7); 27.5 & 27.2, C(β); 26.8 & 26.7, C(γ); 29.0 & 26.3, C(α); 13.57 & 13.55, C(δ); $^{117}$Sn NMR: –204.8 & –215.8; electrospray MS: M/2+Bu$_2$SnOH$^+$(m/z=1001), 40%; Mössbauer: QS: 3.42; IS: 1.34; $\Gamma_1$: 1.22; $\Gamma_2$: 1.18.

Compound 12: triphenyltin 3,6,9-trioxadecanoate, prepared according to method 2, 8 h of reflux, recryst. diethyl ether/methylene chloride, m.p.: 109–111° C., yield 92%, elemental analysis: exp. (calc. for $C_{25}H_{28}SnO_5$): C: 57.1 (56.96); H: 5.4 (5.36);; $^1$H NMR: 7.7–7.8, m, H(o); 7.4–7.5, m, H(m) & H(p); 4.22, s, H(2); 3.7–3.8, m, H(4); 3.6–3.7, m, H(5); 3.5–3.6, m, H(7); 3.4–3.5, m, H(8); 3.34, s, H(10); $^{13}$C NMR: 176.4, C(1); 137.8 C(i); 136.9, C(o) $^2J(^{117/119}Sn-^{13}C)=47$–50; 130.2, C(p) $^4J(^{117/119}Sn-^{13}C)=13$; 128.9, C(m) $^3J(^{117/119}Sn-^{13}C)=63/66$; 72.0, C(8); 70.7, 70.7 & 70.5, C(4), C(5) & C(7); 69.0, C(2); 59.0 C(10); $^{117}$Sn NMR: –103.2; electrospray MS: M+K$^+$(m/z=567), 2%; M+Na$^+$, 11%; M+H$^+$, 6%; Mössbauer: QS: 3.44; IS: 1.29; $\Gamma_1$: 0.91; $\Gamma_2$: 0.87.

Compound 13: tri-n-butyltin 3,6,9-trioxadecanoate, prepared according to method 2, 8 h of reflux, Sephadex LH-20, elution with methylene chloride, liquid, yield 92%;elemental analysis: exp. (calc. for $C_{19}H_{40}SnO_5.\frac{1}{2}H_2O$): C: 47.7 (47.94); H: 8.8 (8.68); $^1$H NMR: 4.09, s, H(2); 3.6–3.8, m, H(4), H(5) & H(7); 3.5–3.6, m, H(8); 3.36, s, H(10);~2, HOH, 1.5–1.7, m, H(β); 1.2–1.4, m, H(α) & H(γ); 0.89, t ($^3J(^1H-^1H)=7$), H(δ); $^{13}$C NMR: 175.1, C(1); 72.0, C(8); 70.6, 70.5 & 70.5, C(4), C(5) & C(7); 69.0, C(2); 58.9, C(10); 27.8, C(β) $^2J(^{117/119}Sn-^{13}C)=20$; 27.0, C(γ) $^3J(^{117/119}Sn-^{13}C)=63/66$; 16.6, C(α) $^1J(^{117/119}Sn-^{13}C)=349/355$; 13.6, C(δ); $^{117}$Sn NMR: 120.7; electrospray MS: M+K$^+$(m/z=507), 18%; M+Na$^+$, 51%; Mössbauer: QS: 3.84; IS: 1.47; $\gamma_1$: 1.07; $\Gamma_2$: 1.02.

Compound 14: di-n-butyltin bis (3,6,9-trioxadecanoate), prepared according to method 3, 12 h of reflux, liquid, yield 95%; elemental analysis: exp. (calc. for $C_{22}H_{44}SnO_{10}$): C: 44.8 (44.99); H: 7.8 (7.56); $^1$H NMR: 4.15, s, H(2); 3.6–3.8, m, H(4), H(5) & H(7); 3.5–3.6, m, H(8); 3.35, s, H(10); 0.6–0.8, m, H(β) & H(α); 1.35, tq ($^3J(^1H-^1H)=7$, $^3J(^1H-^1H)=7$), H(γ); 0.88, t ($^3J(^1H-^1H)=7$), H(δ); $^{13}$C NMR: 175.8, C(1); 71.8, C(8); 71.1, 70.6 & 70.4, C(4), C(5) & C(7); 68.7, C(2); 59.0, C(10); 26.6, C(β), $^2J(^{117/119}Sn-^{13}C)=38$; 26.3, C(γ), $^3J(^{117/119}Sn-^{13}C)=99$; 25.6, C(α), $^1J(^{117/119}Sn-^{13}C)=540/567$; 13.5, C(δ); $^{117}$Sn NMR: –124.1; electrospray MS: M+K$^+$(m/z=627), 12%; M+Na$^+$, 22%; Mössbauer: QS: 3.77; IS: 1.42; $\Gamma_1$: 1.36; $\Gamma_2$: 1.18.

Compound 15: bis[di-n-butyl(3,6,9-trioxadecanoato)tin] oxide, prepared according to method 3, 12 h of reflux, Sephadex LH-20, elution with methylene chloride, liquid, elemental analysis: exp. (calc. for $C_{60}H_{124}Sn_4O_{22}.2H_2O$): C: 42.2 (42.18); H: 7.4 (7.56); yield 80%; $^1$H NMR: 3.96, s, H(2); 3.6–3.7, m, H(4), H(5) & H(7); 3.5–3.6, m, H(8); 3.34, s, H(10);~2, HOH; 1.57, tt ($^3J(^1H-^1H)=7$, $^3J(^1H-^1H)=7$), H(β); 1.4–1.5, m, H(α); 1.27, tq ($^3J(^1H-^1H)=7$, $^3J(^1H-^1H)=7$), H(γ); 0.8–0.9, m, H(δ); $^{13}$C NMR: 175.1, C(1); 72.0, C(8); 70.60, 70.55 & 70.4, C(4), C(5) & C(7); 69.9, C(2); 59.0, C(10); 27.6 & 27.3, C(β); 26.9 & 26.7, C(γ); 29.1 & 25.8, C(α); 13.6, C(δ); $^{117}$Sn NMR: –204.9 & –217.6; electrospray MS: M/2+Na$^+$ (m/z=861), 10%; M/2+Bu$_2$SnOH$^+$, 33%; Mössbauer: QS: 3.49; IS: 1.32; $\Gamma_1$: 0.90; $\Gamma_2$: 0.90.

Stability in Water of Organotin Polyoxaalkanenecarboxylates

The stability in the presence of water of four compounds, 6, 8, 9 and 12, was determined. Solutions in CD$_3$CD$_2$OD exhibit a single resonance in $^{117}$Sn NMR (at 36.5, –210.7, 27.9 and –212.0 ppm, respectively) that is regularly slightly shifted after the addition of increasing amounts of D$_2$O.

Antitumour activity of compounds 1 to 15

The ID$_{50}$ inhibition doses in ng/ml of the tested compounds are given in the table as well as those for some known reference compounds.

|  | MCF-7 | EVSA-T | WiDr | IG-ROV | M19 | A498 | H226 |
|---|---|---|---|---|---|---|---|
| 1 | 15 | 12 | 13 | 30 | 16 | 43 | 37 |
| 2 | 35 | 6 | 11 | 30 | 70 | 97 | 100 |
| 3 | 155 | 128 | 781 | 260 | 219 | 282 | 281 |
| 4 | 36 | 46 | 239 | 82 | 68 | 126 | 73 |
| 5 | <3 | <3 | <3 | <3 | <3 | <3 | <3 |
| 6 | <3 | <3 | <3 | <3 | <3 | <3 | <3 |
| 7 | 273 | 237 | 332 | 321 | 286 | 49 | 854 |
| 8 | 13 | 12 | 34 | 37 | 31 | 32 | 33 |
| 9 | 32 | 40 | 82 | 84 | 90 | 153 | 61 |
| 10 | 60 | 62 | 379 | 128 | 115 | 134 | 161 |
| 11 | <3 | <3 | 6 | <3 | <3 | <3 | 5 |
| 12 | 9 | 9 | 19 | 33 | 24 | 21 | 25 |
| 13 | 36 | 25 | 40 | 89 | 78 | 93 | 56 |
| 14 | 86 | 66 | 495 | 178 | 167 | 145 | 280 |
| 15 | <3 | <3 | 3 | <3 | <3 | <3 | <3 |
| cisplatin | 699 | 422 | 967 | 169 | 558 | 2253 | 3269 |
| doxorubicin | 10 | 8 | 11 | 60 | 16 | 90 | 199 |
| etoposide | 2594 | 317 | 150 | 580 | 505 | 1314 | 3934 |
| 5-fluoro-uracil | 750 | 475 | 225 | 297 | 442 | 143 | 340 |
| methotrexate | 18 | 5 | <3 | 7 | 23 | 37 | 2287 |

Inhibition doses $ID_{50}$ in vitro (in ng/ml) against some tumoural cell lines of human origin, two mammary cancers, (MCF-7, EVSA-T), a colon carcinoma (WiDr), an ovarian cancer (IGROV), a melanoma (M19 MEL), a renal cancer (A498) and a non small cell lung cancer (H226) of organotin derivatives of carboxybenzocrown and di- or trioxaalkanecarboxylic acids, and of some known reference compounds.

What is claimed is:

1. Tin polyoxaalkanecarboxylates having the formula

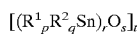

wherein

R$^1$ represents C$_1$–C$_6$ alkyl, branched or straight, or a phenyl group R$^2$ is a carboxylic residue selected from

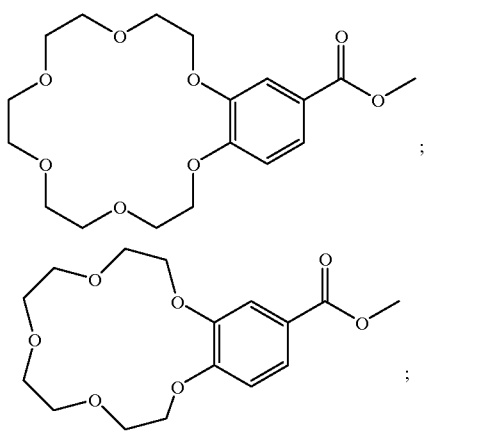

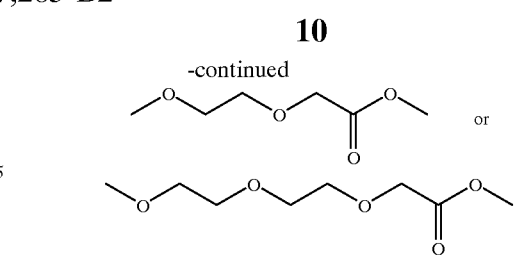

and p, q, r, s and t have the following meanings:

p=3, q=1, r=1, s'0 and t=1;

p=2, q=2, r=1, s'0 and t=1;

or p=2, q=1, r=2, s'1 and t=2.

2. An anti-tumour composition, containing as an active ingredient one or more tin polyoxaalkanecarboxylates of claim 1 of the formula

$R^1{}_3SnR^2$     (1);

$R^1{}_2SnR^2{}_2$     (2);

or

$\{[R^1{}_2R^2Sn]_2O\}_2$     (3), and, when only one said active ingredient is present, a pharmaceutically acceptable carrier.

3. A composition according to claim 2, containing a compound having the formula (1), (2) or (3) as defined in the claim 1, wherein R$^1$ represents a phenylgroup or a n-butylgroup.

4. A compound according to claim 1 of the formula

$R^1{}_3SnR^2$     (1);

$R^1{}_2SnR^2{}_2$     (2);

or

$\{[R^1{}_2R^2Sn]_2O\}_2$     (3).

* * * * *